(12) United States Patent
Kushnir

(10) Patent No.: US 12,415,013 B2
(45) Date of Patent: Sep. 16, 2025

(54) ASSEMBLY AND METHOD FOR THE PREPARATION OF A WOUND DRESSING

(71) Applicant: REDDRESS LTD., Pardes Hana (IL)

(72) Inventor: Igal Kushnir, Pardes Hana (IL)

(73) Assignee: REDDRESS LTD., Pardes Hana (IL)

( * ) Notice: Subject to any disclaimer, the term of this patent is extended or adjusted under 35 U.S.C. 154(b) by 698 days.

(21) Appl. No.: 17/785,203

(22) PCT Filed: Dec. 6, 2020

(86) PCT No.: PCT/IL2020/051254
§ 371 (c)(1),
(2) Date: Jun. 14, 2022

(87) PCT Pub. No.: WO2021/124317
PCT Pub. Date: Jun. 24, 2021

(65) Prior Publication Data
US 2023/0018002 A1    Jan. 19, 2023

Related U.S. Application Data

(60) Provisional application No. 62/949,099, filed on Dec. 17, 2019.

(51) Int. Cl.
*A61L 15/40* (2006.01)
(52) U.S. Cl.
CPC ......... *A61L 15/40* (2013.01); *A61L 2300/418* (2013.01)
(58) Field of Classification Search
USPC .......................................... 424/445

IPC ....................................................... A61L 15/40
See application file for complete search history.

(56) References Cited

U.S. PATENT DOCUMENTS

| | | | | |
|---|---|---|---|---|
| 4,417,981 A | * | 11/1983 | Nugent | B01L 3/50215 422/918 |
| 5,533,518 A | * | 7/1996 | Vogler | G01N 33/491 600/573 |
| 9,180,142 B2 | | 11/2015 | Kushnir | |

FOREIGN PATENT DOCUMENTS

| | | |
|---|---|---|
| WO | 2010086848 A2 | 8/2010 |
| WO | 2019058375 A1 | 3/2019 |

OTHER PUBLICATIONS

International Search Report for corresponding application PCT/IL2020/051254 filed Dec. 6, 2020; Mail date Mar. 15, 2021.
Written Opinion for corresponding application PCT/IL2020/051254 filed Dec. 6, 2020; Mail date Mar. 15, 2021.

* cited by examiner

*Primary Examiner* — Walter E Webb
(74) *Attorney, Agent, or Firm* — CANTOR COLBURN LLP

(57) ABSTRACT

The present disclosure provides a wound dressing assembly comprising (i) a blood-clotting mold device with a mold cavity for forming a molded blood clot for use in dressing a wound. Prior to extraction, the molded blood clot is pushed towards the mold cavity's interior, which causes the molded blood clot to disassociate from the cavity walls and thereafter it can be removed with none or only minimal damage to its integrity.

20 Claims, 6 Drawing Sheets

ASSEMBLY AND METHOD FOR THE PREPARATION OF A WOUND DRESSING

CROSS REFERENCE TO RELATED APPLICATION

This application is related to and claims the benefit of U.S. Provisional Patent Application No. 62/949,099 filed on Dec. 17, 2019, the entire contents of which are incorporated herein by reference.

TECHNOLOGICAL FIELD

This disclosure is in the field of wound treatment and concerns a wound dressing assembly for the preparation of a blood clot and use of this blood clot in wound treatment.

BACKGROUND

Chronic wounds and skin ulcers are a serious medical condition and effective wound treatment approaches is a recognized medical need.

U.S. Pat. No. 9,180,142 discloses a wound treatment procedure by which blood is coagulated and the so-formed blood clot is applied onto a wound with a dressing material. PCT publication WO 2019/058375 discloses a preparation assembly and method for preparing a blood clot-based wound dressing making use of a blood-clotting mold device. For dressing, the blood is clotted in said mold and after clotting, the clotted blood mass is transferred onto a wound.

GENERAL DESCRIPTION

The present disclosure concerns a wound dressing system and method making use of clotted blood in such a dressing. Specifically provided by this disclosure is a wound dressing assembly (e.g. in the form of a kit-of-parts) for preparing such a blood clot, a method for preparing a wound dressing comprising such a blood clot, and a method for dressing the wound therewith.

The blood clot is prepared in a mold device with an enclosure in which the clot is formed. This enclosure will be referred to, herein as "mold cavity" and the blood clot formed therein will be referred to as "molded blood clot".

One of the challenges of the assembly and method of WO 2019/058375 is that the molded blood clot sticks to the walls of the mold cavity and the separation for the purpose of applying it onto a wound without damaging the integrity of the clot is challenging. This challenge is solved, in accordance with the current disclosure, by pushing the clot in a direction towards the interior of the mold cavity (namely in a direction opposite to that in which it extracted for use) whereby the clot separates from the walls of the enclosure without a significant damage to its overall integrity. This pushing is typically the first step after opening the enclosure following the blood clot formation. The molded blood clot can then be easily extracted and removed from the mold device for application onto a wound. By one embodiment such pushing is achieved through the use of an auxiliary device configured for that purpose. The auxiliary device has typically a circumferential, clot-engaging member of dimensions corresponding to those of the mold cavity. By pushing this device against the molded blood clot, it displaces towards the interior of the mold cavity and, consequently, disassociates from its walls. The molded blood clot can then be removed for application onto the wound. The molded blood clot may then be applied onto a wound but may be combined with a dressing material, e.g. a conventional dressing material such as a bandage, gauze, etc., before applying it onto a wound or after.

The molded blood clot that is formed and used according to this disclosure is typically, but not exclusively, formed from blood of the same subject whose wound is to be dressed by the teaching of this disclosure. The blood is typically whole blood withdrawn from the subject in any manner acceptable in medical practice for blood withdrawal. In some other embodiments, the blood is whole blood from a blood bank.

Thus, provided by this disclosure is a method for the preparation of a blood-clot comprising would dressing of the kind described in WO 2019/058375 as well as an assembly of parts for such preparation.

The wound dressing assembly of this disclosure comprises a blood-clotting mold device with mold cavity, defined between walls of a main body and a removable closure (e.g. in the form of a foil, film, lid, panel, etc.) that seals an opening of the cavity, typically hermetically so as to maintain sterility. This device serves, as will be further understood from the description below, as a mold for forming a blood clot that is intended for placing onto a wound. The device is configured to permit introduction of blood into the enclosure, typically without removal of the closure or portion thereof. Such introduction may, for example, be through piercing the walls or the closure of the enclosure with a needle of a syringe and injecting blood from the syringe into the enclosure. Thus, by one embodiment, at least one of the walls or closure of the device is pierceable by a needle and through the pierce formed therewith, blood is introduced into the sealed enclosure.

The assembly also comprises said auxiliary device that is configured for separating the clot from the walls of the cavity. By one embodiment of this disclosure, this is achieved through forcing the clot to inwardly displace into the mold cavity. Such inward displacement causes the clot's peripheral edge to separate from the cavity's inner walls to facilitate subsequent extraction thereof. Said device has, by one embodiment, a circumferential, clot-engaging member of dimensions corresponding to those of the mold cavity for engaging the periphery of the molded blood clot. Said auxiliary device may made of or coated by a material that would not adhere to the clot. By another embodiment said auxiliary device has a plurality of such members, each one engaging another portion of molded blood clot's periphery. The auxiliary device may have a body that can be held by a user with said member or plurality of members configured as circumferential projection or a plurality of circumferential projections for engaging and applying a force on the molded blood clot's periphery. Said member may be, configured, for example, with a tapered end for facilitating the separation of the molded clot's periphery and the walls of the mold cavity. The body of said auxiliary device may be configured as a ring configured about an axis with a planar face with axially projecting annular member of a plurality of such members arranged in an annulus.

After pushing the molded blood clot, as described above, and its consequent dissociation from the walls of the mold cavity, it may be safely removed without, or only minimal damage to its integrity.

The blood is typically whole venous blood withdrawn from the subject.

By an embodiment, the mold cavity has a port for blood introduction; or at times two ports, one for introducing blood and the other for venting (e.g. to permit egress of gas from the enclosure during blood introduction). The venting port may be a priori sealed, intended for removal of excess pressure during injection of the blood into the enclosure. Typically, prior to injection of the blood and in order to permit such venting, the vent is opened.

The mold cavity (prior to introducing the volume of blood), by one embodiment, holds a vacuum.

In some embodiments, the mold cavity comprises a coagulation initiator in an amount sufficient to facilitate coagulation of blood introduced into the enclosure. The coagulation initiator may also be introduced into the mold cavity before or after introducing the blood thereinto and may, thus, be held in an independent container until such introduction. By other embodiments the coagulation initiator is introduced into the mold cavity before or after the introduction of blood. Or by yet another embodiment the coagulation initiator is first mixed with blood and this mixture is then introduced into the mold cavity. The introduction of the blood, and where applicable also the coagulation initiator, may be by the use of a syringe, e.g. through a whole punctured by a needle, which may be the syringe needle.

Blood coagulation initiators are known in the art. In one embodiment of the present disclosure, the blood coagulation initiator comprises kaolin, calcium or both. The blood coagulation initiator (kaolin or any other coagulation initiator) may be provided in any form, such as, liquid, powder, granulate, etc.

Once the blood clot is formed within the enclosure, it may be transferable onto a wound or onto a dressing material.

The assembly preferably comprises a blood clot support matrix, which may be a supporting substrate or a scaffold matrix within the mold cavity, typically held adjacent its opening in close proximity and, at times, in association, with the closure. During formation of the molded blood clot, the support matrix becomes integrated in the clot. The support matrix may have the purpose of (i) providing an overall support to the blood clot, (ii) assisting in maintaining structural integrity of the clot once formed, and/or (iii) enabling the transfer of the clot to the wound or onto a dressing and supporting the clot throughout such transfer. This support matrix is typically in a form of a net, such as a plastic net or a fibrous net, may be a mash, a cloth, etc. In some embodiments, the matrix is of a material similar to that of a dressing material, e.g. gauze.

After introduction of blood into the mold cavity and, where not a priori present, also after introduction of the coagulation initiator, the device may be agitated to mix the blood and the coagulation initiator and then incubated until coagulation and formation of the molded blood clot. Where the assembly comprises a support matrix, the mold device is positioned so that the blood comes into contact with said matrix so that it becomes integrated into the molded blood clot as it forms. In the typical case in which the support matrix device is adjacent the closure, the device is positioned with the closure at its bottom.

The shape of the mold cavity is configured to permit extraction of the formed molded blood clot without compromising the integrity of the blood clot. For this, the opening of the mold cavity, that is initially sealed/closed by the closure, should be wide to permit such extraction, e.g. a shape of a relatively shallow cavity.

The mold device may have different shape and sizes to match different shapes and sizes of wounds.

The mold cavity has a shape and dimension that configures the eventual overall shape of the clotted blood mass formed within the enclosure and hence the shape and dimension of the blood clot subsequently applied onto the wound. The shape and dimension of said cavity (and hence the shape and dimension of the eventual blood clot) may be designed according to the intended use and site of application. For a typical case of application onto a skin wound or ulcer, the mold cavity is typically designed with an opening having a width sufficient to permit relatively easy extraction of the clot as whole without compromising its integrity. The clot is typically formed to have a horizontal dimension that is considerably larger than its height (thickness), e.g. in the form of a relatively shallow cavity as noted above. In some other embodiments, e.g. in the case of a tunneling wound, the relative dimension may be different and configured for such types of wounds.

The mold device may, by some embodiments, have the general form of a blister and the mold cavity being a film that is removable from the rims of the main body. The walls of the mold cavity may be fully transparent or only a portion thereof is transparent.

Further, to facilitate transfer of the formed blood clot, without compromising the integrity of the clot, the mold cavity may be made of or the internal walls coated with a material of the kind to which a blood clot does not adhere or adheres to only weakly.

Also provided by this disclosure is a method for preparing a wound dressing making use of the blood-clotting mold device disclosed herein. Generally, the method comprises injecting a volume of blood into the mold cavity of the of the currently disclosed blood-clotting mold device, permitting the volume of blood to clot to thereby obtain a molded blood clot within the device's enclosure, removing the closure and extracting the blood clot out of the enclosure.

By some embodiments, contemplated within the method of this disclosure, is a procedure by which a wall of the enclosure or the closure is first pierced to form a vent, e.g. by a sharp object or by a needle (e.g. the same needle subsequently used for injection of the blood) and only then blood is injected into the enclosure.

In some embodiments, after extraction, the blood clot may be combined with a dressing material. Such combination may involve transfer of the blood clot onto the dressing material for subsequent placing of the combined blood-clot and dressing material onto a wound; or placing the blood clot directly onto the wound and covering it with the dressing material. The dressing material may be gauze or any other material suitable or commonly used for dressing wounds.

Also provided by this disclosure is a method for dressing a wound. This method comprises the preparation of a blood clot and its extraction, in the manner described above and then applying the extracted blood clot onto a wound. Prior to or after application of the blood clot onto the wound, the blood clot may be combined with a wound dressing material as described above.

The assembly of this disclosure, which may be in the form of a kit-of-parts or a collection of discrete elements combined for use in accordance with this disclosure, can comprise, in addition to the blood-clotting mold device, other elements for use in the methods disclosed herein.

Without being limited thereto, such other elements may include means for transferring the molded blood clot that has been formed in said enclosure onto the wound. Accordingly, in some embodiments, the assembly comprises a blood clot removing tool, e.g. a spoon-like or spatula-like instrument. This tool can be made of plastic, metal, wood, cardboard, silicon, or be made from any other suitable material, and is configured for the removal of the clot from the enclosure preferably in a manner that preserves the clot's structural integrity. In some embodiments, the removing tool is configured also for separating the blood clot from the wall of the enclosure.

In some embodiments, such other elements may comprise (i) means for securing the formed blood clot to the wound, (ii) dressing material, e.g. gauze or any other material that is or may be used in medical practice for dressing wounds, (iii) means for blood withdrawal and collection, (iv) a blood collection vial, (v) a blood coagulant to prevent premature coagulation of the blood (e.g. before introducing into the enclosure), (vi) blood removal and transfer tool; etc.

Reference is also made to U.S. Pat. No. 9,180,142, the relevant portions thereof being incorporated herein by reference.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
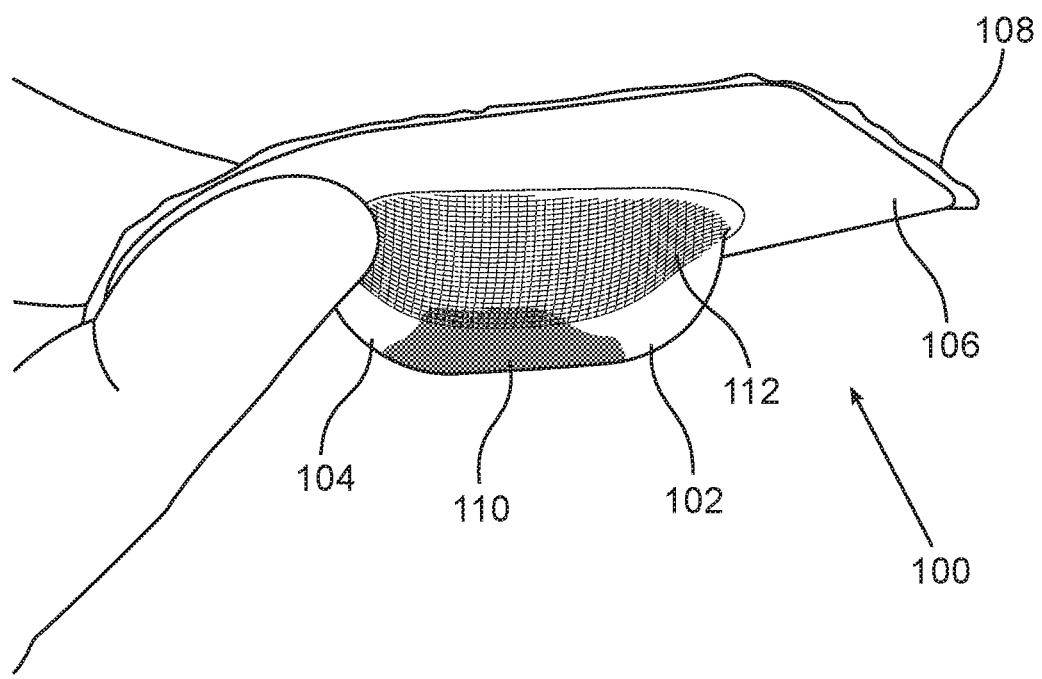
FIG. 1 is a picture of a bottom perspective view of a mold device, according to an embodiment of this disclosure, which is in the form of a blister.

The embodiments illustrated in the annexed drawings include an enclosure in the form of a blister, which is an exemplary embodiment of the broader context of the present disclosure. Thus, this description of specific embodiments is intended for illustration of the more general principle of this disclosure and is not intended to be limiting. The disclosure of the specific embodiment below Referring first to FIG. 1, shown is a picture of a mold device generally designated 100 and in the form of a blister, having a main body 102 with a depression constituting the mold cavity 104 and a flat rim 106. Fitted onto the rim is a removable closure 108 in the form of a laminate/film. Contained within the enclosure 100 is a coagulating initiator substance 110 which may be in the form of a liquid, powder, granulate, etc. Also contained in the enclosure is a blood clot-supporting (scaffold) matrix 112 which may be made of gauze, of a polymeric mesh, etc., held at its peripheral portions between the rim and the closure and having a central portion within the enclosure.

The mold device is part of an assembly, e.g. in the form of kits of parts, that comprises also an auxiliary device such as that illustrated in FIGS. 2A-2E. The assembly may also include other elements such as blood withdrawal components for extraction of venous blood from the patient, one or more syringes, one or needles, gauze or other dressing material, plasters, a container with a coagulation initiator in addition or in alternative to that comprised within the mold cavity (element 110). The coagulation initiator may, for example, be kaolin.

The auxiliary device 200 shown in FIGS. 2A-2E has an annular body 202 that can be held by the user; and an annular, clot-engaging member 204 projecting from body 202. Clot-engaging member 204 has dimensions corresponding to those of the mold cavity for engaging the periphery of the molded blood clot; namely the projections trace the periphery of mold cavity. As can be seen, body 202 defines planar shoulders 206 extending peripherally from the base of member 204 in FIG. 2C and member 204 extends essentially normal from the plane defined by shoulders 206. As can best be seen in FIG. 2E, the projection, is constituted by a flap internally folded to define a tapered end 208.

As can also be noted, the peripheral wall 210 of the clot-engaging member 204 is slightly slanted off a full normal orientation. The tapering, the flap-based structure and the slight off-normal orientation allow the clot-engaging member 204 to gently separate the molded blood clot formed within the mold cavity 104 from the cavities wall, while pushing it in the direction of the cavity's interior, with the flexibility to trace the converging walls of the mold cavity.

Figures 2A, 2B:
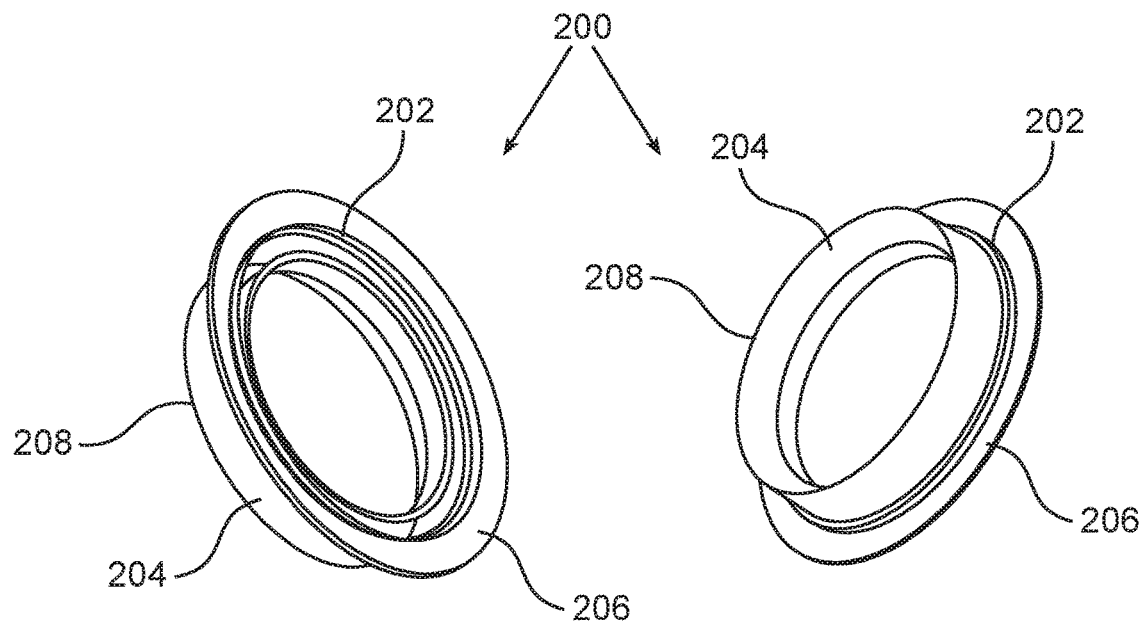
FIG. 2A-2E show a drawings of an auxiliary device according to an embodiment of this disclosure including, respectively, a top perspective view, a bottom perspective view, a side view, a top view and a cross-section through lines A-A in in FIG. 2D.
Figures 2C, 2D, 2E:
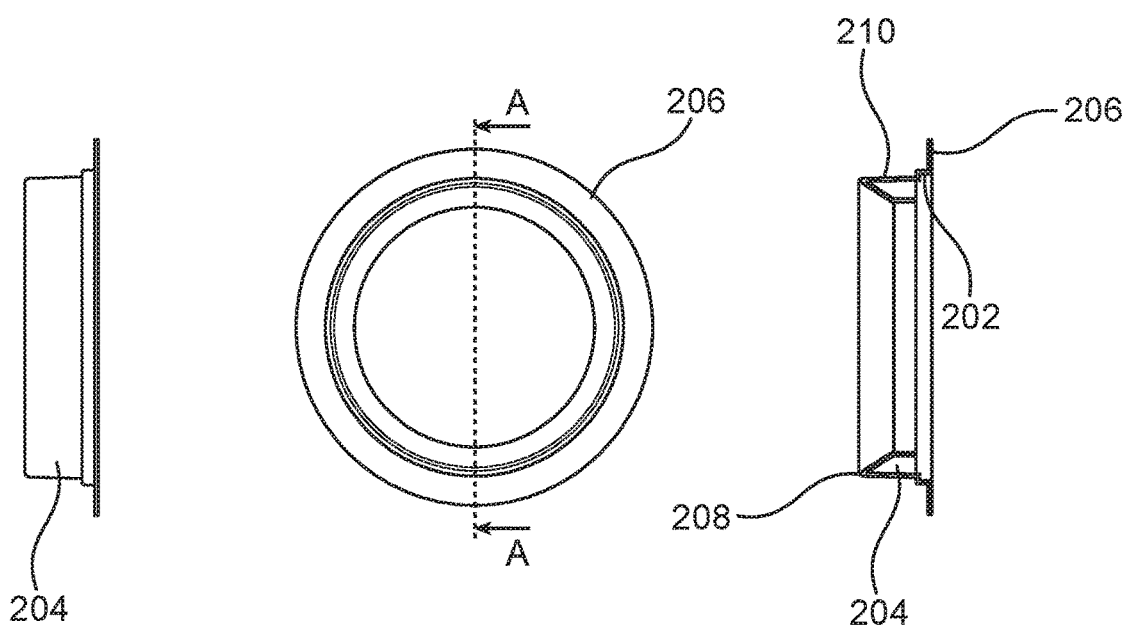
Figure 3A:
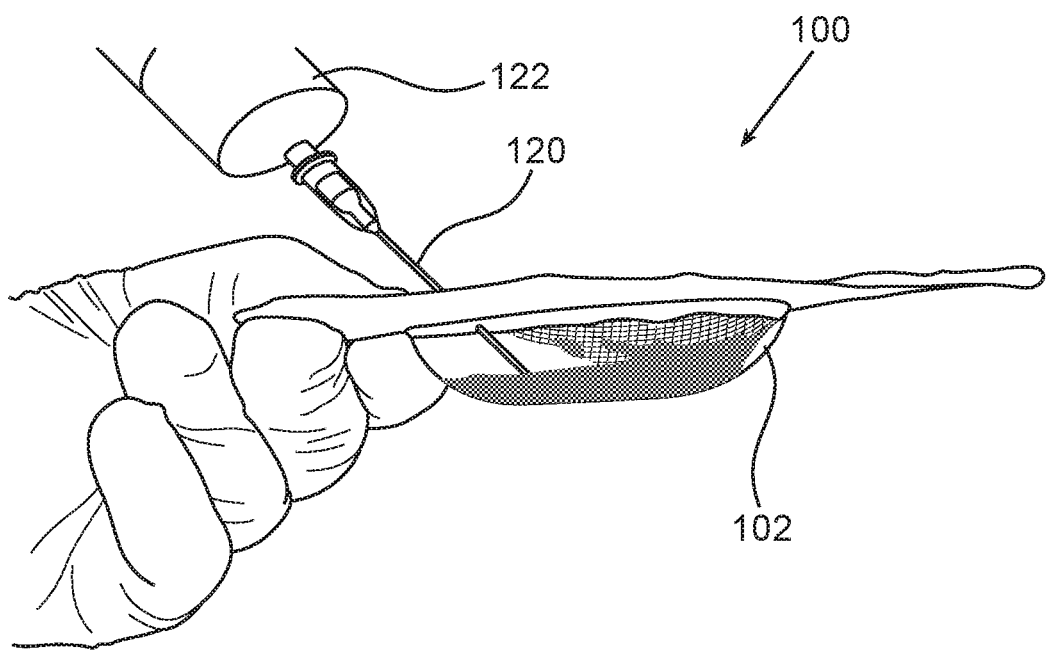
FIGS. 3A and 3B are pictures of side perspective views showing the injection of blood into the mold cavity.
Figure 3B:
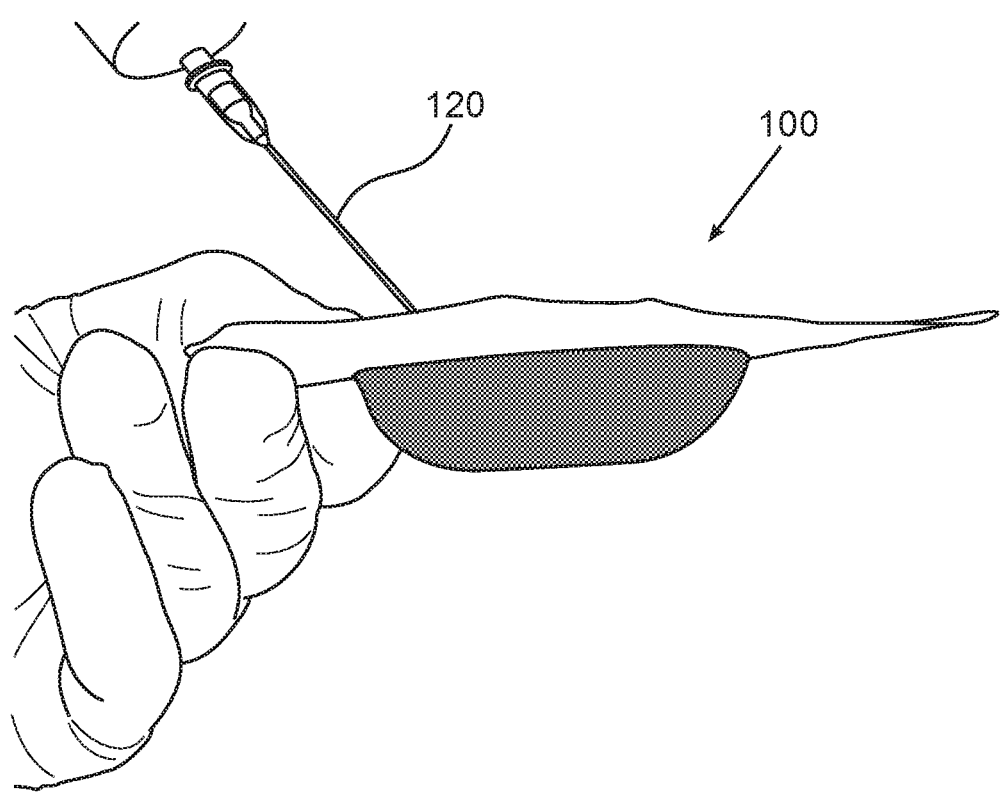

Blood, typically whole blood, is withdrawn and then injected into the mold cavity, as shown in FIGS. 3A and 3B. Specifically, a needle 120 of a syringe 122 that contains the whole blood pierces the closure 108 and blood is injected until it fills a significant portion of the enclosure, sufficient to cover the support matrix 112, as seen in FIG. 2B. It is possible, also, to initially pierce the closure so as to form a vent opening, e.g. by the blood injection needle, and inject the blood only subsequently. In some embodiments, a blood coagulation initiator is already a priori present in the mold cavity, as in the case of the embodiment of FIG. 1. In other embodiments, a coagulation initiator is introduced into the mold cavity before or after the introduction of the blood. The device is typically agitated to mix the blood and the coagulation initiator and is incubated for a time sufficient to permit blood coagulation and the formation of the molded blood clot. During incubation the mold device would be best placed on top of closure 108 to permit integration of the support matrix into the molded blood clot.

Figure 4A:
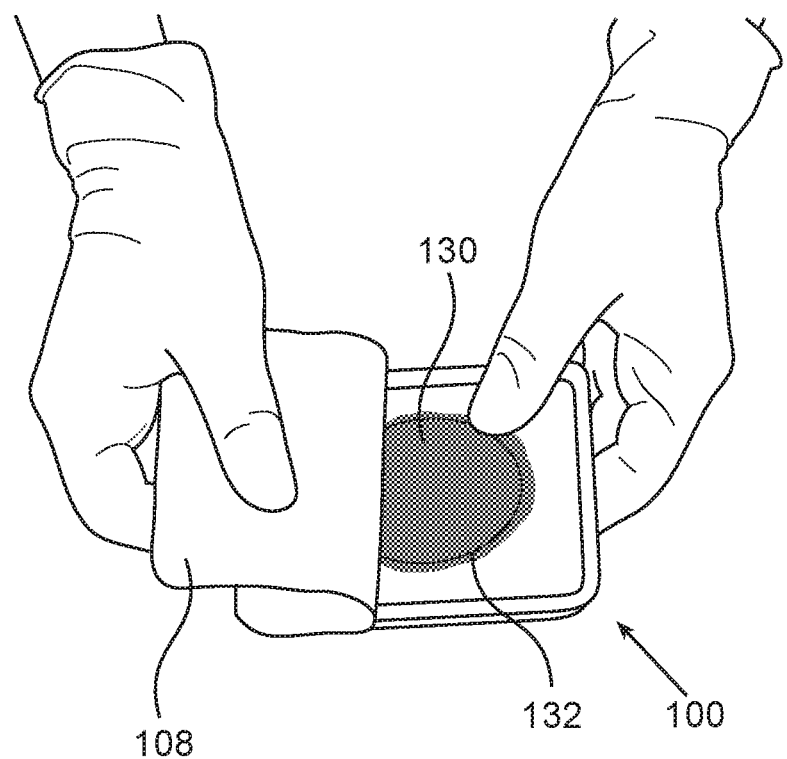
FIGS. 4A and 4B are shows the removal of the closure revealing the molded blood clot formed within the mold cavity.
Figure 4B:
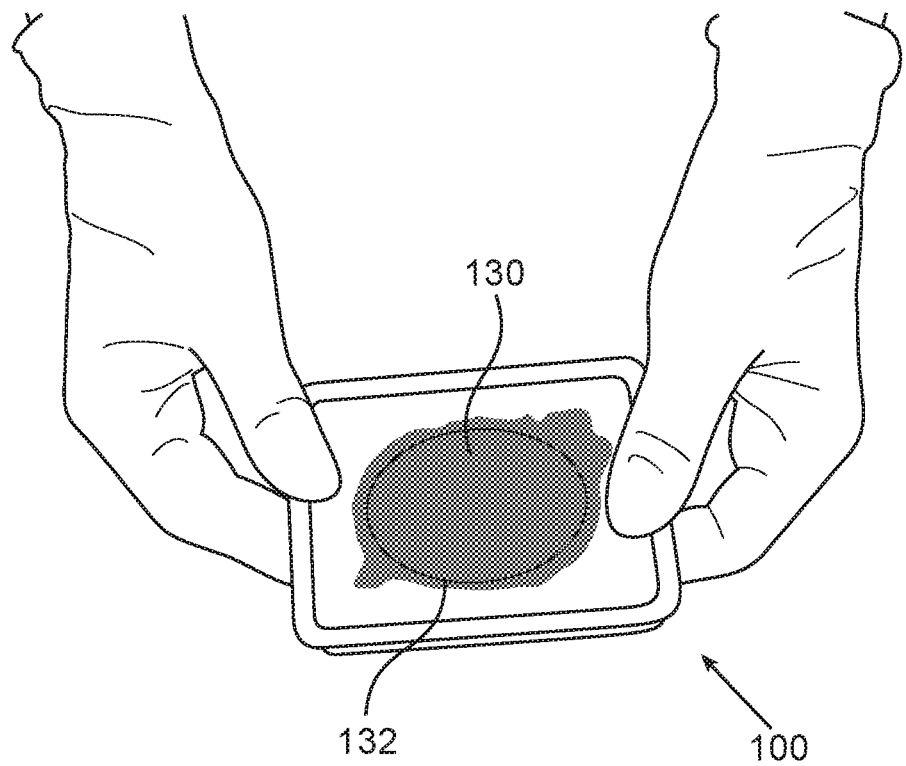
Figure 5A:
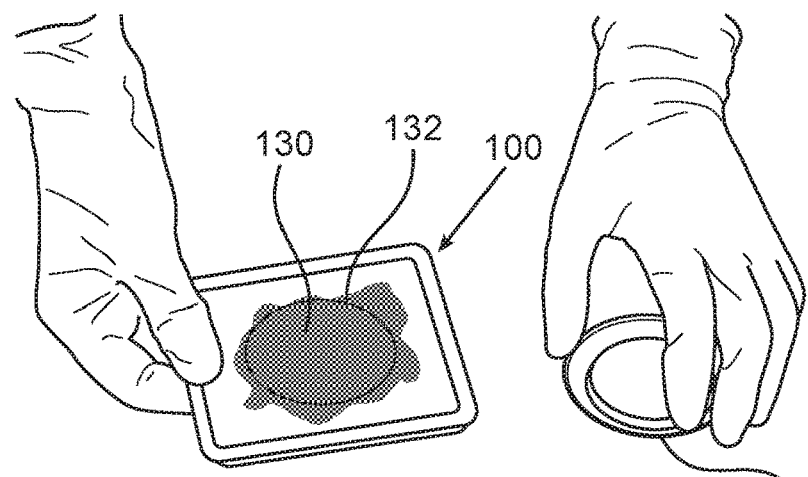
FIG. 5A-5C shows the manner in which an auxiliary device, according to an embodiment of this disclosure, is used to push the molded blood clot towards the interior of the mold cavity to thereby free the molded blood clot from the walls of the mold cavity.

As can be seen in FIGS. 4A and 4B, after incubation, the closure 108 is removed revealing the molded blood clot 130, as best seen in FIG. 4B and FIG. 5A. The molded blood clot may be integrated with the support matrix, the peripheral portions of which 132 extend peripheral to the molded blood clot.

Figure 5B:
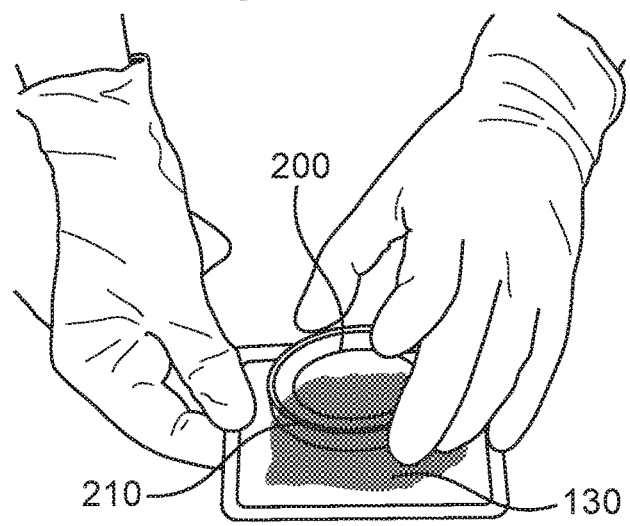
Figure 5C:
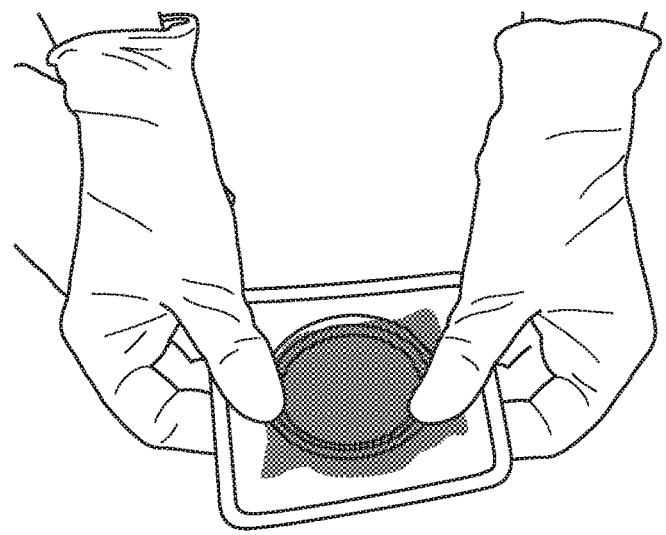
Figure 6A:
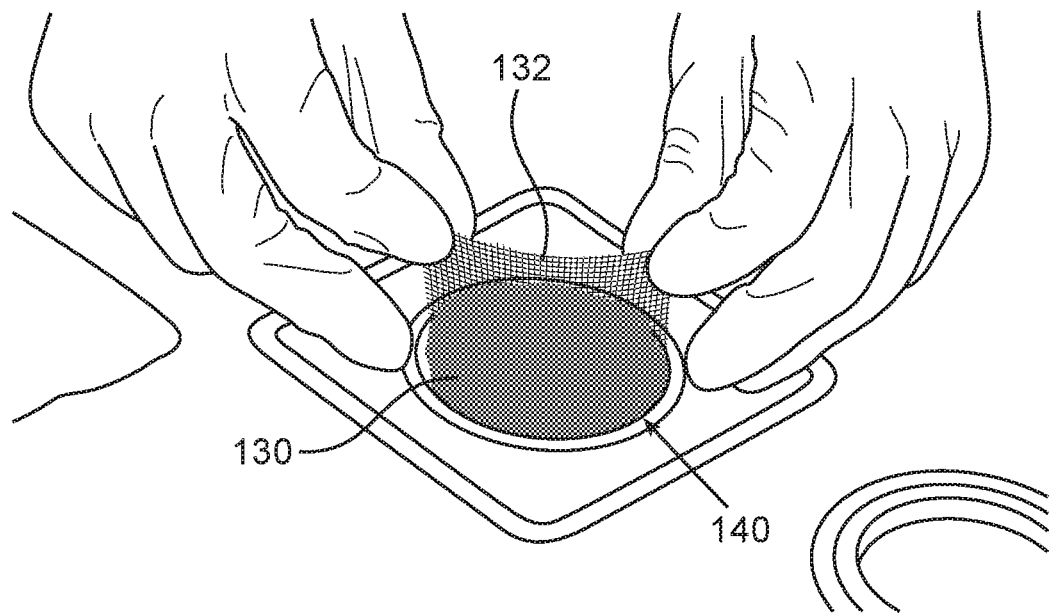
FIGS. 6A and 6B show the manner of extraction of the molded blood clot from the mold cavity.
Figure 6B:
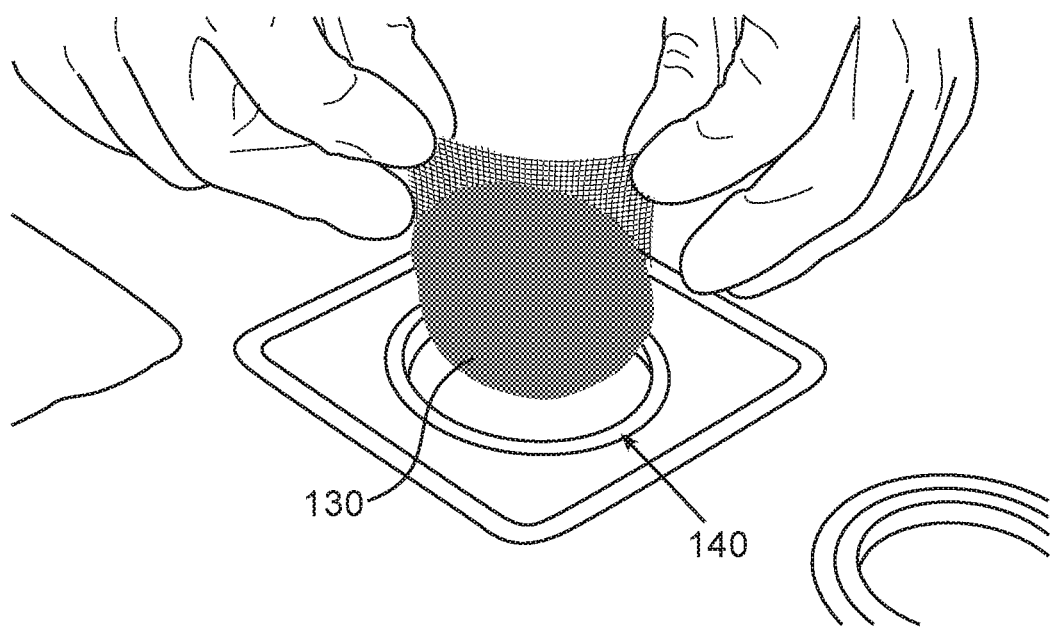

As can be seen in FIGS. 5A-5C, the auxiliary device 200, can then be taken (FIG. 5A) and pushed against the clot with the blood engaging member 210 facing the molded blood clot 130 (FIG. 5B) and after fully pushing the auxiliary device against the molded blood clot (FIG. 5C) the clot edges become separated from the walls of the mold cavity. As can be seen in FIGS. 6A and 6B, the molded blood clot 130 can then be removed from the mold cavity through the cavity's opening 140, by holding the matrix's peripheral portions 132.

The invention claimed is:
1. An assembly for preparing a blood clot-comprising wound dressing, the assembly comprises a blood-clotting mold device having a mold cavity defined between walls of a main body and a removable closure over an opening and is configured for introduction of blood thereinto, a coagulation initiator in an amount sufficient to coagulate blood introduced into the enclosure to form a molded blood clot, and an auxiliary device configured for pushing the molded blood clot in a direction towards the interior of the mold cavity.

2. The assembly of claim 1, wherein said auxiliary device has a circumferential clot engaging member.

3. The assembly of claim 2, wherein said clot-engaging member has dimensions corresponding to those of the mold cavity for engaging the periphery of the molded blood clot.

4. The assembly of claim 2, wherein said member projects from a body of said device.

5. The dressing assembly of claim 1, wherein said coagulation initiator is comprised within the mold cavity, wherein at least one of the walls of the mold cavity and closure is pierceable by needle, and wherein the mold cavity contains a blood-clot support matrix.

6. A method for preparing a wound dressing, comprising:
introducing a volume of blood into a mold cavity of a blood-clotting mold device;
maintaining the blood within the enclosure for a time sufficient to permit clotting of the blood to thereby obtain a molded blood clot;
removing said closure to open the mold cavity;
pushing the molded blood clot in a direction towards the mold cavity's interior to thereby separate the molded blood clot's periphery from walls of the mold cavity; and
extracting the blood clot from the mold cavity and combining it with a wound dressing material.

7. The method of claim 6, wherein said pushing is carried out with an auxiliary device configured for that purpose.

8. The method of claim 7, wherein said auxiliary device has a circumferential clot engaging member.

9. The method of claim 8, wherein said clot-engaging member has dimensions corresponding to those of the mold cavity for engaging the periphery of the molded blood clot.

10. The method of claim 8, wherein said member projects from a body of said device.

11. The method of claim 10, comprising combining the blood clot onto a dressing material.

12. The method of claim 8, wherein the mold cavity comprises a blood clot-support matrix and said clotting causes said matrix to become integrated within the molded blood clot, where said extracting comprises removal of the clot with said matrix, wherein at least one of (i) the walls of the mold cavity and (ii) the removable closure, is pierceable by a needle, and wherein said introducing comprises piercing at least one of the wall and closure and injecting the blood therethrough.

13. The method of claim 8, wherein the closure is a removable film, wherein the enclosure has the general shape of a blister, and wherein the enclosure is first pierced to form a vent and then the blood is injected.

14. A method for dressing a wound, comprising:
introducing a volume of blood into a mold cavity of a blood-clotting mold device;
maintaining the blood within the enclosure for a time sufficient to permit clotting of the blood to thereby obtain a molded blood clot;
removing said closure to open the mold cavity;
pushing the molded blood clot in a direction towards the mold cavity's interior to thereby separate the molded blood clot's periphery from walls of the mold cavity;
extracting the blood clot from the mold cavity and combining it with a wound dressing material; and
fixing the blood clot onto the wound.

15. The method of claim 14, wherein said pushing is carried out with an auxiliary device configured for that purpose.

16. The method of claim 15, wherein said auxiliary device has a circumferential annular, clot engaging member.

17. The method of claim 16, wherein said clot-engaging member has dimensions corresponding to those of the mold cavity for engaging the periphery of the molded blood clot.

18. The method of claim 15, wherein said member projects from a body of said device.

19. The method of claim 14, further comprising combining the blood clot onto a dressing material,
wherein the mold cavity comprises a blood clot-support matrix and said extracting comprised removal of the clot with said matrix,
wherein said fixing is with a dressing material,
wherein the mold cavity comprises a blood clot-support matrix and said clotting cause said matrix to become integrated within the molded blood clot, and
wherein said extracting comprises removal of the clot with said matrix.

20. The method of claim 14, wherein at least one of (i) the walls of the mold cavity and (ii) the removable closure, is pierceable by a needle, wherein said introducing comprises piercing at least one of the wall and closure and injecting the blood therethrough, wherein the closure is a film that is removably adhered to rims of the enclosure walls, wherein the enclosure has the general shape of a blister, and wherein the enclosure is first pierced to form a vent and then the blood is injected into the enclosure.

* * * * *